United States Patent [19]
Edwards

[11] Patent Number: 4,945,477
[45] Date of Patent: Jul. 31, 1990

[54] MEDICAL INFORMATION SYSTEM

[75] Inventor: D. Craig Edwards, Bellevue, Wash.

[73] Assignee: First Medic, Bellevue, Wash.

[21] Appl. No.: 111,985

[22] Filed: Oct. 22, 1987

[51] Int. Cl.$^5$ .............................................. A61N 1/36
[52] U.S. Cl. ........................... 364/413.06; 128/419 D
[58] Field of Search ......................... 364/415, 413.06;
128/702, 705, 692, 419 D, 419 S

[56] References Cited

U.S. PATENT DOCUMENTS

| | | | |
|---|---|---|---|
| 4,216,462 | 8/1980 | McGrath et al. | 364/415 |
| 4,295,474 | 10/1981 | Fischell | 128/692 |
| 4,417,306 | 11/1983 | Citron et al. | 128/702 |
| 4,506,677 | 3/1985 | Lambert | 128/692 |
| 4,576,170 | 3/1986 | Bradley et al. | 128/419 D |
| 4,610,254 | 9/1986 | Morgen et al. | 128/419 D |
| 4,614,192 | 9/1986 | Imran et al. | 128/419 D |
| 4,622,979 | 11/1986 | Katchis et al. | 128/702 |
| 4,785,812 | 11/1988 | Phil et al. | 128/696 |
| 4,800,883 | 1/1989 | Winstrom | 128/419 D |

FOREIGN PATENT DOCUMENTS 8202836  9/1982  PCT Int'l Appl. ............. 128/419 D

*Primary Examiner*—Jerry Smith
*Assistant Examiner*—Kim Thanh T. Bui
*Attorney, Agent, or Firm*—Seed and Berry

[57] ABSTRACT

A medical information system. Data from electrodes are digitized and received by a microprocessor which causes them to be stored in a memory in accordance with a predetermined priority scheme. The data stored in the memory means can be read out to a monitor, a printer, or another computer for further processing.

16 Claims, 8 Drawing Sheets

HEARTSTART 2000    RUN REPORT

REPORT DATE ___/___/___                TECHNICIANS _____

EPISODE DATE . . . . . . .11 FEB 87      PART NUMBER . . . . . . 900050
EPISODE DATE . . . . . 17 : 44 : 19      SERIAL NUMBER . . . . . 000447
SELF CHECK . . . . . . . . . . . OK      SOFTWARE VERSION . . . . . 10
CONFIGURATION . . . . SEMI-AUTO          MCU S.W. VERSION . . . . . . . 4

↖ 50

EVENT LOG:                                              52
──────────  DATE: 11 FEB 87                             ↙
17 : 44 : 19   UNIT ON
17 : 44 : 22   UNIT OFF
17 : 44 : 26   UNIT ON
17 : 44 : 35   "CHECK PATIENT" MESSAGE GIVEN - TREATABLE RHYTHM DETECTED
17 : 44 : 36   START ANALYSIS
17 : 44 : 40   START CHARGING
17 : 44 : 43   COMMIT TO TREAT
17 : 44 : 48   READY TO SHOCK
17 : 44 : 50   SHOCK NUMBER 1 DELIVERED, 200 JOULES
17 : 44 : 59   START ANALYSIS
17 : 45 : 06   SHOCK NOT INDICATED
17 : 45 : 21   "CHECK PATIENT" MESSAGE GIVEN - TREATABLE RHYTHM DETECTED
17 : 45 : 24   START ANALYSIS
17 : 45 : 28   START CHARGING
17 : 45 : 31   COMMIT TO TREAT
17 : 45 : 36   READY TO SHOCK
17 : 45 : 37   SHOCK NUMBER 2 DELIVERED, 200 JOULES
17 : 45 : 46   START ANALYSIS
17 : 45 : 50   START CHARGING
17 : 45 : 53   COMMIT TO TREAT
17 : 46 : 06   READY TO SHOCK
17 : 46 : 09   SHOCK NUMBER 3 DELIVERED, 360 JOULES
17 : 46 : 22   "CHECK PATIENT" MESSAGE GIVEN - TREATABLE RHYTHM DETECTED
17 : 46 : 26   START ANALYSIS
17 : 46 : 33   SHOCK NOT INDICATED
17 : 46 : 33   UNIT OFF

SER. NO. 000447    EPISODE DATE: 11 FEB 87    TIME: 17 : 44 : 19    PAGE 1

*Figure 3A*

SHOCK NUMBER 1 DATA
TIME DELIVERED . . . . . 17 : 44 : 50           BATTERY . . . . . GOOD
ENERGY DELIVERED . . 200 JOULES           IMPEDANCE . . 52 OHMS

17 : 44 : 52                    17 : 44 : 55

17 : 44 : 58                    17 : 45 : 01

Start Analysis

17 : 45 : 22                    17 : 45 : 25

Start Analysis

17 : 45 : 28                    17 : 45 : 31

Start Charging                 Commit to Treat

SER. NO. 000447   EPISODE DATE: 11 FEB 87   TIME: 17 : 44 : 19   PAGE 3

SHOCK NUMBER   2 DATA
TIME DELIVERED . . . . . 17 : 45 : 37         BATTERY . . . . . GOOD
ENERGY DELIVERED . . 200 JOULES              IMPEDANCE . . 52 OHMS

17 : 45 : 40                    17 : 45 : 43

17 : 45 : 46                    17 : 45 : 49

Start Analysis                  Start Charging

17 : 45 : 52                    17 : 45 : 55

Commit to Treat

17 : 45 : 58                    17 : 46 : 01

SER. NO. 000447   EPISODE DATE: 11 FEB 87   TIME: 17 : 44 : 19   PAGE 4

SHOCK NUMBER 3 DATA
TIME DELIVERED . . . . . 17 : 46 : 09        BATTERY . . . . . GOOD
ENERGY DELIVERED . . 360 JOULES        IMPEDANCE . . 54 OHMS

Start
Analysis

END REPORT -- MEDICAL CONTROL MODULE READY FOR REUSE

SER. NO. 000447   EPISODE DATE: 11 FEB 87   TIME: 17 : 44 : 19   PAGE 5

MEDICAL INFORMATION SYSTEM

TECHNICAL FIELD

This invention relates to a system for gathering and presenting information pertaining to a medical event, and more particularly, to a system for gathering and presenting information pertaining to an out-of-hospital cardiac medical emergency to concerned medical professionals.

BACKGROUND ART

In the past, information concerning medical emergencies has been gathered in a variety of ways. Usually, a written report is completed by the technical personnel involved. This report is based on details concerning the sequence of events and the patient condition and progress from the time of arrival of the personnel until the patient's arrival at the hospital. It is also based on other information pertinent to this out-of-hospital event, including electronic signals indicative of the patient's medical state. Naturally, during the medical emergency, it is difficult to write down any relevant information that is not recorded. This means that much of the information needed to complete a report about the emergency must be recalled by the personnel involved in the emergency. In addition, any information that is recorded, for example, on a paper strip chart recorder, must be fully reviewed to be edited for the significant events and be correlated with non-recorded procedures applied to the patient.

Typically, the medical training of the personnel who treat the patient and report on the treatment ranges between 100 and 2000 hours. This represents a wide variety of skill in treatment and in the gathering of information, which can lead to inconsistent reporting of the medical emergency.

After the patient and attending technicians arrive at the hospital, the receiving physician often requires accurate information about the patient's condition as soon as possible. This need for information is particularly important in a cardiac emergency, where proper care must often be provided very quickly and where treatments such as defibrillation are often administered during the trip to the hospital.

In addition to these considerations, there are often legal requirements for providing reports concerning the medical emergency. The attending technician is usually allowed to practice certain medical procedures based on state laws and under standing orders from a physician who is responsible for medical control. Thus, in order to provide for acceptable medical control, the responsible physician must review the medical emergency in detail. This typically requires the physician to review the written reports, the patient's records, and other sources of information. Often the physician will find it necessary to interview the technician and/or other personnel to obtain an accurate understanding of the care provided to the patient.

One common method for gathering information and generating such reports is by using a tape recorder. Typically, such a tape recorder is attached to a piece of equipment that is used in the emergency, and pertinent information is recorded. In a cardiac emergency, the tape recorder can be attached to the defibrillator or a monitor and both the electrocardiogram (EKG) signal and the technician's voice recorded. The physician can then listen to the voices on the tape and make copies of the important and interesting portions of the recorded EKG signal. Unfortunately, this method requires a significant amount of a physician's time and effort to sort out the information to determine the care given to the patient.

DISCLOSURE OF THE INVENTION

It is an object of the present invention to provide a medical information system capable of automatically preparing a report of a patient's medical state in an out-of-hospital situation.

It is another object of the present invention to provide a medical information system capable of storing information related to a medical emergency.

It is still another object of the present invention to provide a medical information system capable of simultaneously recording both a signal representative of a patient's medical state and notations of the treatment provided to the patient.

Yet another object of the present invention is to provide a medical information system that can record relevant medical information and later provide a human-readable report of that stored medical information.

These and other objects are provided by the medical information retrieval system of the present invention, which is used for receiving, compiling, and storing data relating to the medical state of a patient. The medical information system comprises means for producing a signal indicative of the patient's medical state, memory means for storing data, and an elapsed-time clock for measuring time elapsed since the receipt of a start signal. In addition, the medical information system comprises a microprocessor connected to the means for producing the patient's medical state signal, the memory means, and the elapsed-time clock, and adapted to receive and sample the medical state signal and generate a start signal in response to one or more first predetermined conditions in the sampled medical state signal. The microprocessor is further adapted to store samples of the medical state signal and the respective elapsed times of occurrence in the memory means in response to one or more second predetermined conditions in the sampled medical state signal. The samples are stored in accordance with a predetermined priority scheme. In a further embodiment, the medical information system can comprise means for producing a human-readable output from the stored data.

In yet another embodiment, a medical information system can further comprise means for entering commands to the microprocessor, the commands being stored in the memory means as an activity record. The medical information system can record and report episode data, relating an event to its actual time of occurrence. Finally, the medical information system can include means for receiving the memory into which the data have been stored and reading out the data in a human-readable form.

BRIEF DESCRIPTION OF THE DRAWINGS

FIGS. 3A–3E are representative samples of an output produced by a human-readable output device.

BEST MODE FOR CARRYING OUT THE INVENTION

Figure 1:
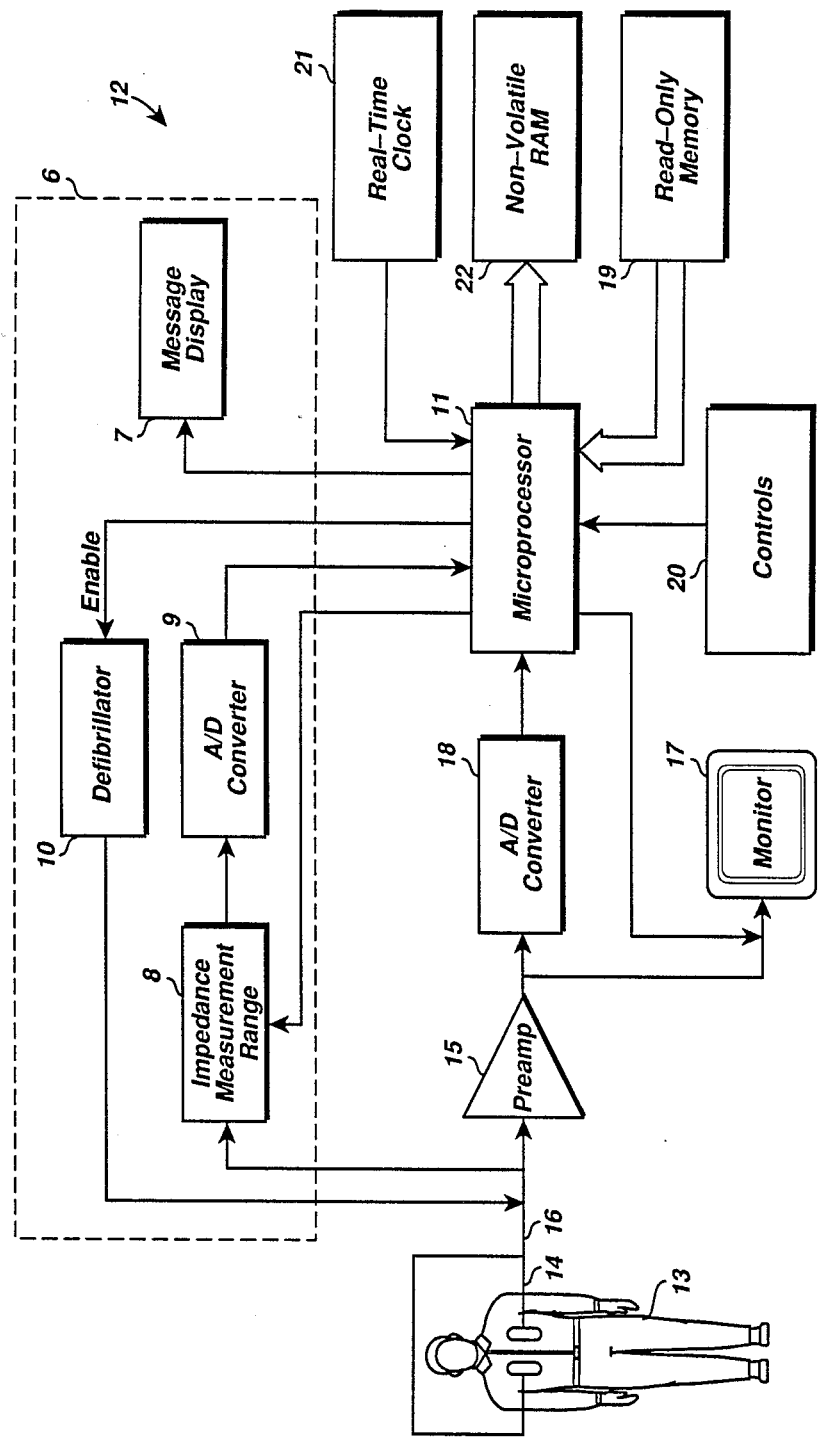
FIG. 1 is a block diagram of a medical information system adapted to receive and store medical state signals and activity records in conjunction with a medical emergency.

The medical information system of the present invention can be operated in conjunction with a defibrillation unit of the type described in co-pending U.S. patent application Ser. No. 935,248, assigned to the assignee of the present application. The defibrillation unit, which can operate in manual, semiautomatic or automatic modes, is capable of interacting with the medical information system. The system components in FIG. 1 that are used only with the defibrillation unit are contained in the area designated by reference numeral 6. These components are message display 7, impedance measurement unit 8, analog-to-digital (A/D) converter 9, and defibrillator 10. Microprocessor 11, used with both the defibrillation unit and medical information system 12, generates signals that tell whether the defibrillation unit is in its ANALYZE mode or its MONITOR mode, whether the defibrillation unit is prepared to administer a shock, and what the values of various parameters are (for example, the recommended energy level of a shock to be administered). The defibrillation unit accepts control signals from medical information system 12, such as commands to enter either the ANALYZE mode or the MONITOR mode, and what level of shock should be administered, and when to administer the shock.

It will be understood by those skilled in the art that the present medical information system can, with appropriate modifications to its software, interact with medical signal sources (other than a defibrillation unit) that indicate a particular medical state.

Figure 3B:
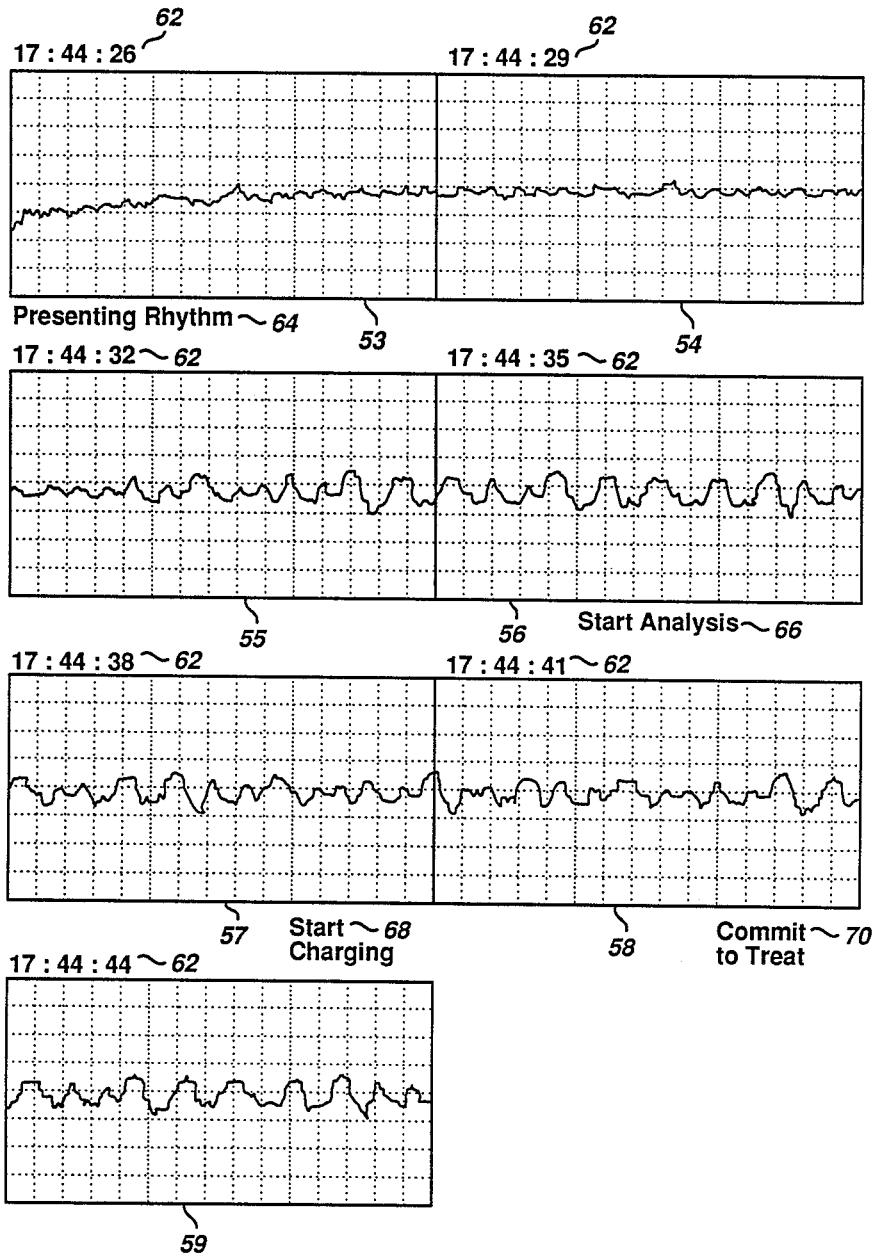
Figure 3C:
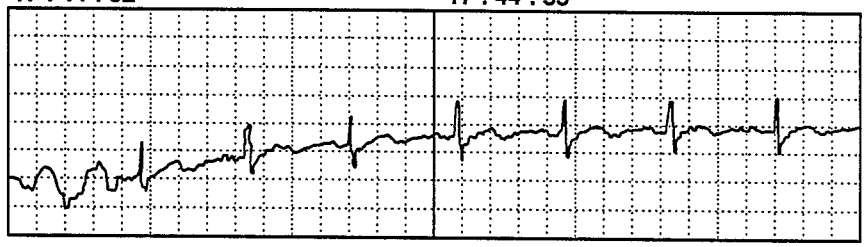
Figure 3C:
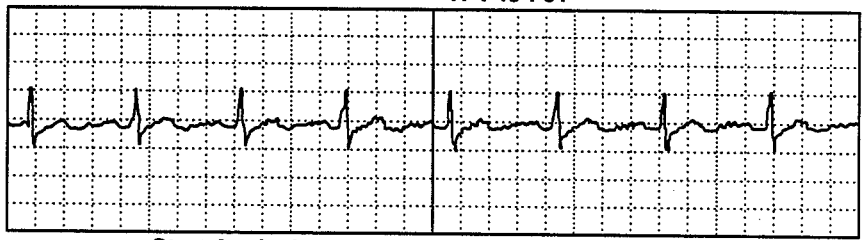
Figure 3C:
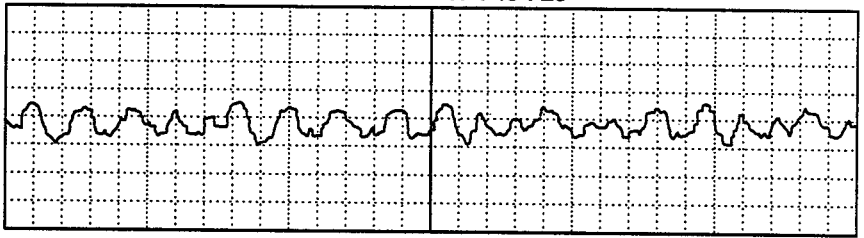
Figure 3C:
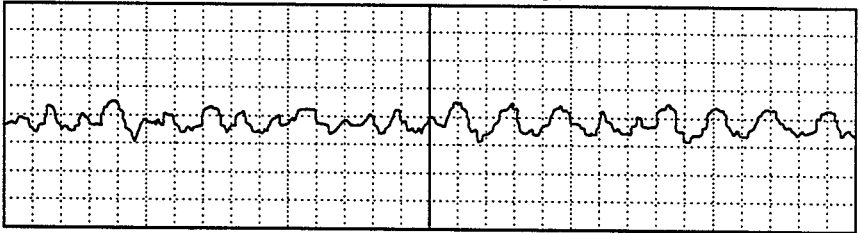
Figure 3D:
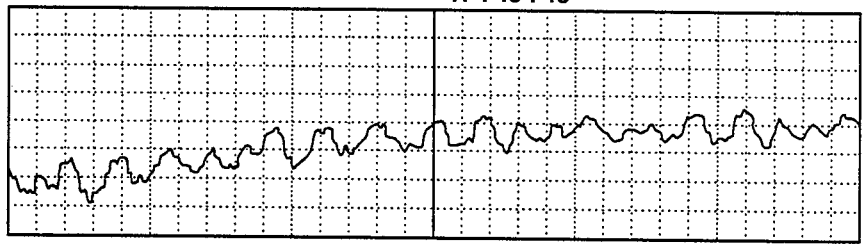
Figure 3D:
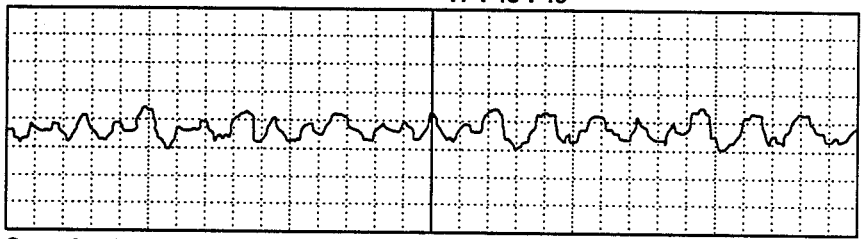
Figure 3D:
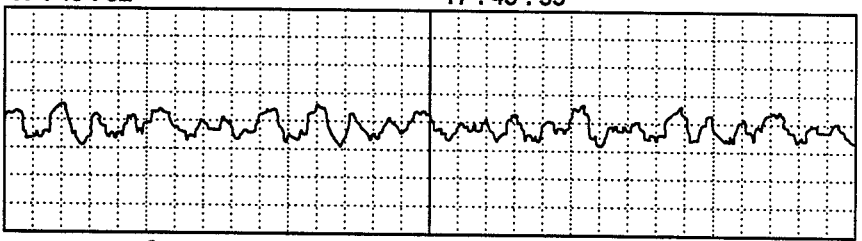
Figure 3D:
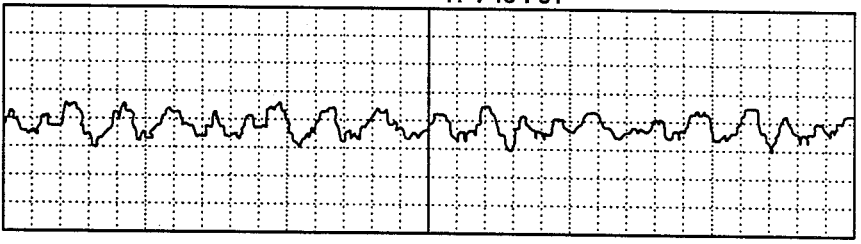
Figure 3E:
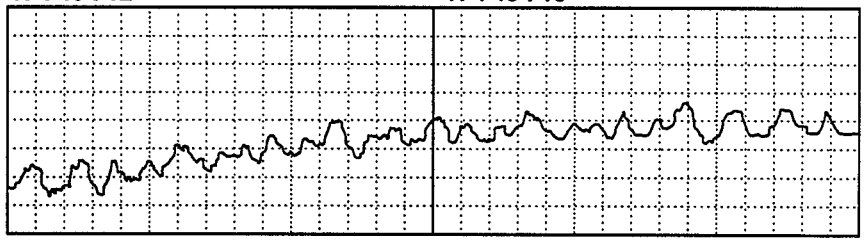
Figure 3E:
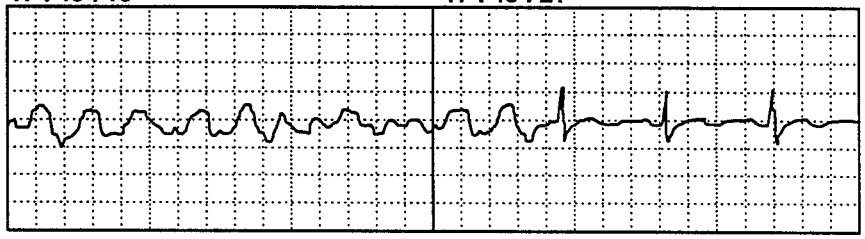
Figure 3E:
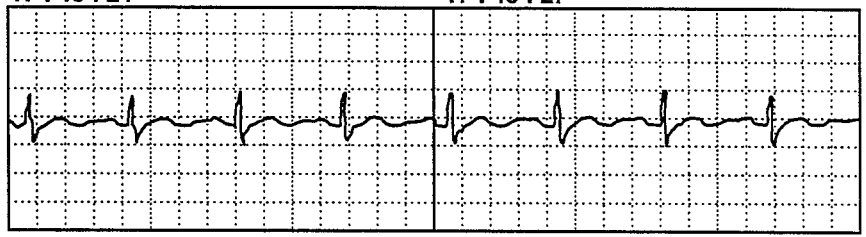

A patient 13, who may be experiencing a medical emergency related, for example, to a cardiac condition, is being monitored by conventional electrocardiograph (EKG) electrodes 14. The electrical signal produced by the EKG electrodes 14 is received by preamplifier 15 over cable 16. Preamplifier 15 amplifies the low-level analog signal on cable 16 to a level that can be displayed on a monitor 17 along with alphanumeric symbols that can, for example, specify the measurement conditions. The signal from the preamplifier 15 is also received by an analog-to-digital (A/D) converter 18, which forms digital samples of the amplified signal relating to the medical state of patient 13. This digitized signal is sent to microprocessor 11, which operates according to a program contained in a read-only memory (ROM) 19. The program controls the interactions between the medical information system and the defibrillation unit. Additional traces showing the operation of the defibrillator are illustrated in FIGS. 3C–E.

Microprocessor 11 can also receive signals from controls 20. Controls 20 are activated by an operator in order to cause certain operations to occur within the medical information system or certain data to be stored. Among the signals that can be activated from controls 20 (containing, for example, a membrane keyboard) are ANALYZE and MONITOR signals. The ANALYZE signal is generated if the ANALYZE button on controls 20 is pressed. If the ANALYZE button is not pressed, then the MONITOR signal is generated. These signals cause the defibrillator to enter a corresponding mode. Controls 20 also contain an ENERGY SELECT button for choosing the energy level of the shock to be administered to the patient, a SHOCK button for causing microprocessor 11 to enable defibrillator 10 to administer the shock to patient 13, and possibly a keyboard or bar code input device for inputting information relating to the patient, such as the patient's name, address, age, special medical conditions, etc. In addition, microprocessor 11 receives a signal from real-time clock 21. The real-time clock signal can comprise digital data to be stored with digitized samples of the patient's medical state signal in a memory 22, such as a nonvolatile, random access memory (RAM).

A/D converter 18 can be caused to produce samples every ten milliseconds for a period of three seconds. This produces 300 digital samples that can be stored in non-volatile RAM 22, under the control of microprocessor 11. The medical state signal can be an EKG signal.

Memory 22 can be caused to store up to 50 three-second segments of medical state sample data (i.e., 15,000 individual signal samples). In addition, memory 22 can be caused to receive and store data relating to any activation of controls 20, data from additional sensors, such as battery voltage sensors, and data relating to individual episodes, such as their real time of occurrence.

After microprocessor 11 has stored 50 episodes (i.e., 150 seconds) of EKG samples in memory 22, the microprocessor institutes a priority scheme, by which it determines which episodes of EKG data will be retained in memory 22. The data with the lowest priority are overwritten in the memory by new, higher priority data. The data given the highest priority are the presenting rhythm (i.e., the first nine seconds after the medical information system has been turned on and the impedance of electrodes 14 determined to be acceptable).

The data given the second highest priority in storage are the EKG samples taken around the first defibrillation shock. All three-second EKG segments from the time that the ANALYZE button in controls 20 is pressed until fifteen seconds after the defibrillation pulse is delivered will be stored.

Third priority is given to EKG samples taken around the last occurring defibrillation shock. In this case, all three-second EKG segments between the time of activation of the ANALYZE button in controls 20 are stored until fifteen seconds after the last defibrillation pulse is delivered are also stored.

Fourth priority is given to EKG samples taken around the second defibrillation shock, then those around the third defibrillation shock, and so forth. These stored three-second EKG segments include those from the time the ANALYZE button in controls 20 is pressed until fifteen seconds after the defibrillation pulse is delivered.

The fifth priority for storage in memory 22 is given to the three-second intervals following activation of the ANALYZE switch in controls 20 that did not result in a shock being delivered to patient 13.

Last priority for data stored in memory 22 is given to six-second samples taken once each minute while the medical information system is in the MONITOR mode.

In addition to the medical information signal data stored in connection with each signal segment, other data stored are episode annotations, such as the time and date that the episode started, identification of the presenting rhythm (in the case that the signal is an EKG), and the unit serial number. Also stored with the EKG segment data are activity record annotations, such as times of occurrence (to the nearest second) of pressing the ANALYZE button, the ENERGY SELECT button, or the SHOCK button of controls 20. Other data that are recorded are the inter-electrode impedance just prior to defibrillation, the energy value of the shock to be delivered, the time at which the MONITOR mode was entered, and the reason why. Further data stored in an activity record are summaries of the analyses done while the medical information system is in the MONITOR and ANALYZE modes. Data from the MONITOR mode include the number of analyses that resulted in shock, non-shock, or noise.

Figure 2:
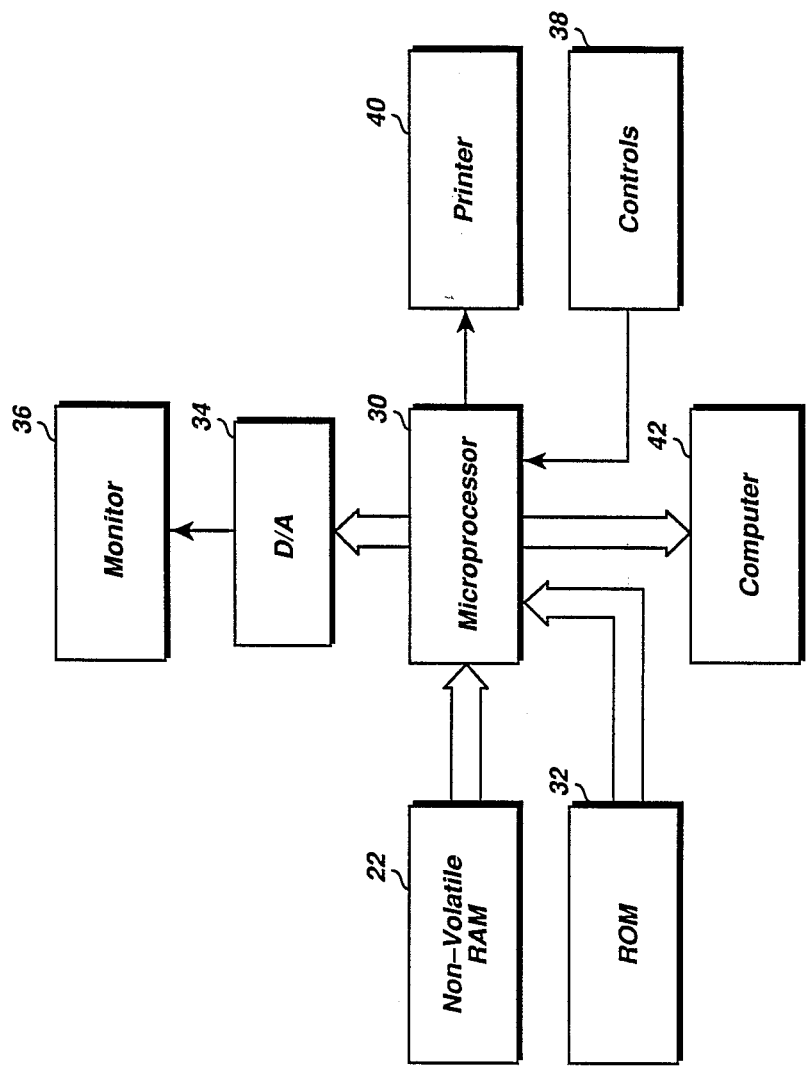
FIG. 2 is a block diagram of an apparatus for receiving a memory in which has been stored a medical state signal and activity record data and for providing a human-readable record therefrom.

After appropriate EKG sample data, support data, and annotations have been stored in memory 22 by the apparatus of FIG. 1, memory 22 can be removed from that apparatus and connected to the apparatus shown in FIG. 2. Memory 22 connects to a second microprocessor 30, which is operating according to a program stored in second ROM 32. Data are read from memory 22 and converted to a form appropriate for display by microprocessor 30, which transmits the resulting digital data to digital-to-analog (D/A) converter 34. D/A converter 34 produces an analog signal that can be sent to a viewable terminal device, such as a monitor 36. Microprocessor 30 can also be caused, by activation of appropriate buttons in controls 38, to transmit data representing the data stored in memory 28 to printer 40. Alternatively, by depressing an appropriate button in controls 38, microprocessor 30 can be caused to send digital data to a conventional computer 42 for further processing.

FIGS. 3A–3E show examples of human-readable representations of the data stored in memory 22 of FIG. 2.

With reference to FIG. 3A, the human-readable report first includes a "Run Report" 50, including such information as the report date and the names of the technicians who operated the medical information system during the event that is being reported. Other data include the date and time of the emergency, the defibrillator serial number, the status of the system after it has performed a self-check, and the configuration of the defibrillation circuit used in connection with the present medical information system.

An "Event log" 52 is printed immediately below the Run Report. The Event log is a chronological record of the important events in the operation of the unit. It shows the times that the machine is turned on and off, when various operator messages are displayed, when the operator commands are given, and when various activities in the operation of the unit, such as the delivery of a shock, occur.

The report then follows with a series of EKG traces, shown in FIGS. 3B–E. Each three-second EKG segment is labeled with its actual beginning time 62. Each EKG segment can also be labeled with activity records, such as those designated by numerals 64–70.

The data shown in EKG segments 53–55 represent the EKG samples taken when the machine is first turned on. According to the priority scheme maintained by microprocessor 11 in FIG. 1, this presenting data is given the highest priority. The ANALYZE button in controls 20 is then depressed during segment 56. This time is indicated by activity record 66—"Start Analysis." In the next three-second EKG segment 55, the capacitor of the defibrillation unit is charging, as indicated by activity record 68. During the period of analysis represented by the first three EKG segments, the data collected are analyzed and a decision to recommend that a shock be applied is made immediately after the EKG segment 58. This time is indicated by activity record 70—"Commit."

In a semiautomatic defibrillation unit, the next event is to prompt the unit's operator to depress the "SHOCK" button in the controls 20 to administer the shock to the patient 10. The time when the SHOCK button is pressed is indicated by "Event Record" (FIG. 3A). The resulting effect on the EKG signal can readily be seen by reference to EKG segment 59. As also indicated by Event Record 52, the operator has pressed the ANALYZE button immediately after the shock is administered (see EKG segment 58 in FIG. 3B). Nine seconds later, the analysis has determined that a shock to the patient is not indicated and the defibrillator enters the MONITOR mode. This is designated by annotation record 76.

The human-readable report of FIG. 3 contains a summary of shock data relating to the first episode. The summary is designated by numeral 78, and summarizes information relating to the conditions under which the shock is administered.

The shock data are followed by monitor mode data, designated by numeral 80. These data are a summary of the indications provided by the medical information system while it is in the MONITOR mode.

FIG. 3C shows a later sequence of EKG segments, wherein the patient's cardiac activity has reverted to a state of fibrillation. In this case, the medical information system is in the MONITOR mode, as designated by annotation record 82. For example, by the time 12:06:36, the medical information system has determined that the patient's heart has resumed fibrillation and caused a prompting "CHECK PATIENT" message to be displayed to the user of the fibrillation unit, stating that a shock is indicated. In response, the user has initiated the ANALYZE mode by pressing the ANALYZE button in controls 20 (see FIG. 1). This is designated by annotation record 84.

As shown by activity record 86, the user of the defibrillation unit has responded to the prompt by pressing the ANALYZE button in controls 20. The user has also initiated a charging cycle for the defibrillator capacitor, as indicated by annotation record 88. Activity record 90 shows that the user has elected to administer a 360-Joule shock, and, in annotation record 92, a "shock indicated" message is displayed.

The user has pressed the SHOCK button in controls 20 at the same time that activity record 94 is displayed in FIG. 3D and has initiated the ANALYZE mode at the time indicated by activity record 96.

Normal cardiac activity, shown after the shock has been administered, as indicated by activity record 94, continues for the remainder of the time shown in FIGS. 3D and 3E. Annotation record 98 shows that the analysis started at 12:07:01 has determined that a shock is not indicated, and informs the user that the medical information system is entering its MONITOR mode.

Following the report on the second episode, a summary of shock data relating to the second episode is presented, as indicated at 100. These data include information regarding the shock that has been delivered.

As a final step, the medical information system provides an event log 102 with a summary of all activity and annotation records and their times of occurrence.

Figure 4:
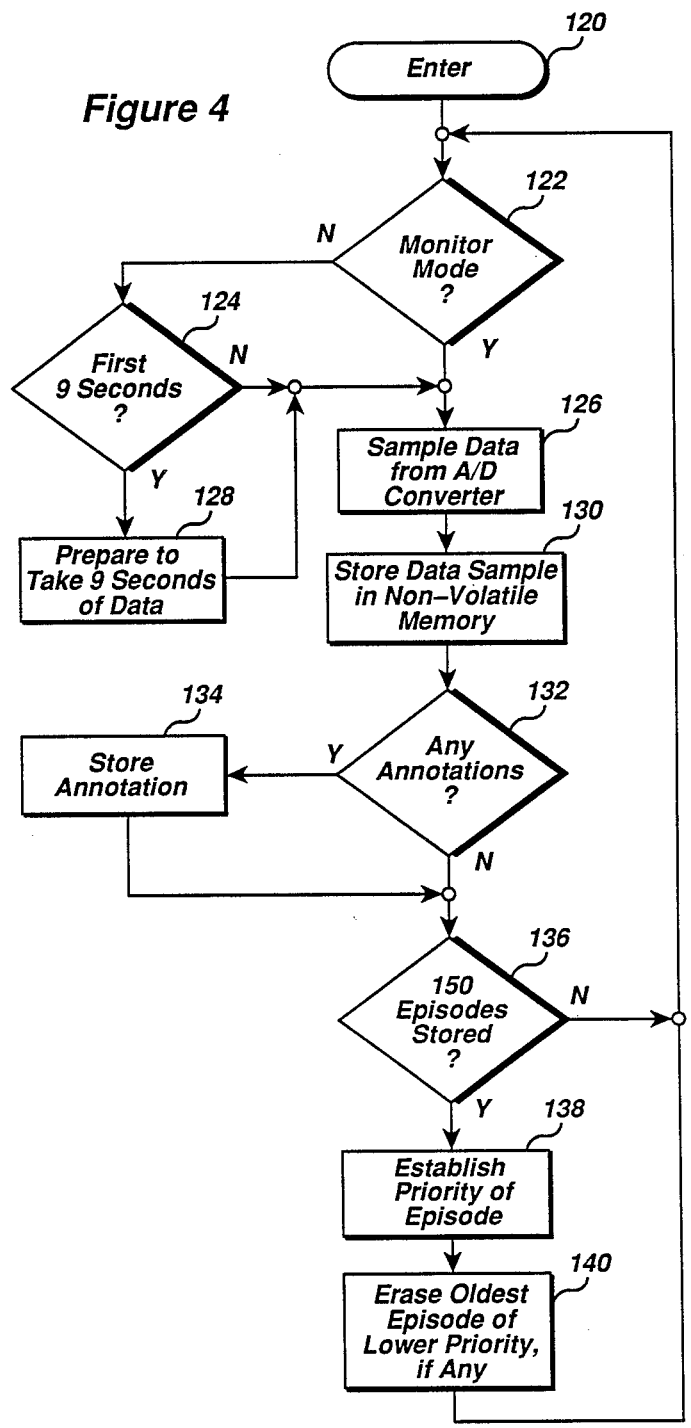
FIG. 4 is a flow chart of a computer program which controls the storage of samples of medical state signals and related annotations by the system of FIG. 1.

FIG. 4 is a flow chart of a computer program which controls the storage of samples of medical state signals and related annotations by the system of FIG. 1. After entering the program through block 120, microprocessor 11 (see FIG. 1) determines whether the medical information system is the MONITOR mode in accordance with a command entered through controls 20 (block 122). If the system is not in MONITOR mode, the program control shifts to decision block 124, which determines whether the medical information system is in its first nine seconds of operation. If it is not, control returns to block 126, where sample data are taken from A/D converter 18. If the medical information system is still in its first nine seconds of operation, microprocessor 11 is configured (through, for example, proper setting of countdown registers) to take further data (block 128). Control then returns to block 126.

After data are sampled from A/D converter 18, the data are stored in nonvolatile memory 22 (block 130). Next, the computer program causes microprocessor 11 to determine whether any annotations, resulting from either an activity record or an episode, have been created since the last sample was taken.

Those skilled in the art of computer programming will recognize that the occurrence of such annotations can be signaled by, for example, interrupts that result from pressing a button in controls 20. Other annotations can result from recognition by a computer program that a medical event (for example, arrhythmia) requiring defibrillation has occurred. If an annotation is recognized by decision block 132, control passes to block 134, where the annotation is stored in nonvolatile memory 22. Otherwise, control passes from decision block 132 to decision block 136, where the program determines whether 150 three-second episodes have been stored in nonvolatile memory 22. If fewer than 150 episodes have been stored, control of the program returns to decision block 122 to receive further sampled data from A/D converter 18. If, on the other hand, 150 episodes of data have been stored in nonvolatile memory 22, control passes to block 138, where the priority of the most recently sampled episode is established. Episode priority has been defined above. The record program then moves to block 140, which causes microprocessor 11 to erase the oldest episode of lowest priority stored in nonvolatile memory 22. The next oldest episode is moved into the portion of memory 22 just erased, followed by a similar shifting of the next episode data, and so forth, until space is made available in memory 22 in the area dedicated to storing the most recently recorded episode. The episode most recently sampled is then stored in this area. If no episodes having a lower priority than the most recently sampled episode are stored in memory 22, this most recent episode data are not stored in memory 22 and will be overwritten when the next episode data samples are taken. Control of the program then returns to decision block 122.

While the preceding detailed description is illustrative of the use of the present medical information system with a manual, automatic or semiautomatic defibrillation system, it will be apparent to those skilled in the art that various other signals representative of a patient's medical state can be used with a medical information system of this sort. While various other modifications of the medical information system of this invention will be apparent to those skilled in the art, the scope of this invention is to be limited only by the following claims.

I claim:

1. A medical information recording system for use with a patient having a medical state, said system receiving and storing data relating to the medical state of said patient, comprising:
   monitor means for producing a monitoring ECG signal indicative of the patient's medical state;
   analysis means for analyzing said ECG signal to determine if a defibrillation shock is indicated; defibrillator means for applying a defibrillator shock to said patient;
   sampling means for obtaining samples of said monitoring signal, said samples having respective characteristics;
   memory means for storing said samples, said memory means having a capacity limited to storing a predetermined number of said samples; and
   processing means connected to said sampling means and said memory means for storing said samples in said memory means, said processing means further including prioritizing means operative whenever the number of samples obtained by said sampling means exceeds the storage capacity of said memory means, said prioritizing means overwriting previously obtained samples stored in said memory means with subsequently obtained samples, depending upon the characteristics of said previously and subsequently obtained samples.

2. The medical information recording system of claim 1 wherein presenting samples obtained when said monitor initially produces said monitoring signal have the highest priority and are stored in said memory means and never overwritten with subsequently obtained samples.

3. The medical information recording system of claim 2 wherein samples obtained contemporaneously with a defibrillation shock first applied to said patient have a second priority and are stored in said memory means as long as said presenting samples do not fill said memory means, and wherein said samples obtained contemporaneously with a first defibrillation shock applied to said patient are never overwritten with subsequently obtained samples.

4. The medical information recording system of claim 3 wherein samples obtained contemporaneously with a defibrillation shock last applied to said patient have a third priority and are stored in said memory means as long as said samples obtained contemporaneously with a defibrillation shock first applied to said patient do not fill said memory means, and wherein said samples obtained contemporaneously with a defibrillation shock last applied to said patient are never overwritten with subsequently obtained samples.

5. The medical information recording system of claim 4 wherein samples obtained contemporaneously with defibrillation shocks applied to said patient intermediate said first and last defibrillation shocks have respective priorities that decrease in chronological order and are stored in said memory means as long as said samples obtained contemporaneously with an intermediate defibrillation shock previously applied to said patient do not fill said memory means, and wherein said samples obtained contemporaneously with a defibrillation shock last applied to said patient are never overwritten with subsequently obtained samples.

6. The medical information recording system of claim 5 wherein said monitor means is an automatic or semiautomatic defibrillator in which an operator can cause the analysis means to analyze the patient's ECG to determine whether defibrillation is indicated, and wherein said processing means causes samples obtained when said analysis means is analyzing said patient's ECG and a defibrillator shock is not subsequently applied to said patient to have priorities that are lower than the samples obtained contemporaneously with said intermediate defibrillation shocks, said processing means storing said samples obtained when said analysis means is analyzing said patient's ECG and defibrillator shock is not subsequently applied to said patient in said memory means as long as said samples obtained contemporaneously with an intermediate defibrillation shock previously applied to said patient do not fill said memory means, and wherein said processing means causes said samples obtained when said analysis means is analyzing said patient's ECG and a defibrillator shock is not subsequently applied to said patient to be never overwritten with subsequently obtained samples unless said subsequently obtained samples are obtained contemporaneously with said intermediate defibrillation shocks.

7. The medical information recording system of claim 1, further including a real-time clock for generating data indicative of the current date and time, and wherein said processing means causes said data to be recorded in said memory means along with contemporaneous samples selected for recording in said memory means by said prioritizing means.

8. An automatic or semiautomatic defibrillator, comprising:
a pair of defibrillator electrodes;
defibrillator means for applying a defibrillator shock to said electrodes in response to a trigger signal;
monitor means for obtaining an ECG signal corresponding to the patient's ECG;
analysis means for analyzing the ECG of a patient to whom said electrodes are connected to determine if a defibrillation shock is indicated;
initiation means for automatically generating or allowing manual generation of said trigger signal in the event that said analysis means determines that a defibrillation shock is indicated;
sampling means for obtaining samples of said ECG signal, said samples having respective characteristics;
memory means for storing said samples, said memory means having a capacity limited to storing a predetermined number of said samples;
processing means connected to said sampling means and said memory means for storing said samples in said memory means, said processing means further including prioritizing means operative whenever the number of samples obtained by said sampling means exceeds the storage capacity of said memory means, said prioritizing means overwriting previously obtained samples stored in said memory means with subsequently obtained samples, depending upon the characteristics of said previously and subsequently obtained samples; and
display means for providing a visually perceivable record of said ECG signals corresponding to said stored samples.

9. The defibrillator of claim 8 further including sensing means for sensing events relating to the operation of said defibrillator and wherein said processing means further causes said memory means to store data indicative of said events.

10. The defibrillator of claim 9 wherein the events relating to the operation of said defibrillator that are sensed by said sensing means are events initiated by an individual operating said defibrillator.

11. The defibrillator of claim 8 wherein presenting samples obtained when said monitor initially produces said monitoring signal have the highest priority and are stored in said memory means and never overwritten with subsequently obtained samples.

12. The defibrillator of claim 11 wherein samples obtained contemporaneously with a defibrillation shock first applied to said patient have a second priority and are stored in said memory means as long as said presenting samples do not fill said memory means, and wherein said samples obtained contemporaneously with a first defibrillation shock applied to said patient are never overwritten with subsequently obtained samples.

13. The defibrillator of claim 12 wherein samples obtained contemporaneously with a defibrillation shock last applied to said patient have a third priority and are stored in said memory means as long as said samples obtained contemporaneously with a defibrillation shock first applied to said patient do not fill said memory means, and wherein said samples obtained contemporaneously with a defibrillation shock last applied to said patient are never overwritten with subsequently obtained samples.

14. The defibrillator of claim 13 wherein samples obtained contemporaneously with defibrillation shocks applied to said patient intermediate said first and last defibrillation shocks have respective priorities that decrease in chronological order and are stored in said memory means as long as said samples obtained contemporaneously with an intermediate defibrillation shock previously applied to said patient do not fill said memory means, and wherein said samples obtained contemporaneously with a defibrillation shock last applied to said patient are never overwritten with subsequently obtained samples.

15. The defibrillator of claim 14 wherein said processing means causes samples obtained when said analysis means is analyzing said patient's ECG and a defibrillator shock is not subsequently applied to said patient to have priorities that are lower than the samples obtained contemporaneously with said intermediate defibrillation shocks, said processing means storing said samples obtained when said analysis means is analyzing said patient's ECG and defibrillator shock is not subsequently applied to said patient in said memory means as long as said samples obtained contemporaneously with an intermediate defibrillation shock previously applied to said patient do not fill said memory means, and wherein said processing means causes said samples obtained when said analysis means is analyzing said patient's ECG and a defibrillator shock is not subsequently applied to said patient to be never overwritten with subsequently obtained samples unless said subsequently obtained samples are obtained contemporaneously with said intermediate defibrillation shocks.

16. The defibrillator of claim 8, further including a real-time clock for generating data indicative of the current date and time, and wherein said processing means causes said data to be recorded in said memory means along with contemporaneous samples selected for recording in said memory means by said prioritizing means.

* * * * *